United States Patent [19]

Ferraro et al.

[11] Patent Number: 4,489,722

[45] Date of Patent: Dec. 25, 1984

[54] LASER RESISTANT ENDOTRACHEAL TUBE

[75] Inventors: Rick J. Ferraro; Henry W. Lynch, both of Racine, Wis.

[73] Assignee: Medical Engineering Corporation, Racine, Wis.

[21] Appl. No.: 424,753

[22] Filed: Sep. 27, 1982

[51] Int. Cl.³ .............................................. A61M 16/00
[52] U.S. Cl. .................................. 128/207.15; 604/96
[58] Field of Search ...................... 128/207.14, 207.15, 128/202.29, 203.12, 203.13, 203.15, 203.23, 203.24, 203.29, 206.29; 604/93–101; 138/DIG. 3, 145, 153, 172

[56] References Cited

U.S. PATENT DOCUMENTS

| 3,854,484 | 12/1974 | Jackson | 128/207.15 |
| 4,090,518 | 5/1978 | Elam | 128/207.15 |
| 4,166,467 | 9/1979 | Abramson | 128/207.14 |
| 4,378,796 | 4/1983 | Milhaud | 128/207.55 |

FOREIGN PATENT DOCUMENTS

| 2426344 | 9/1977 | Fed. Rep. of Germany | 128/207.15 |
| 2463624 | 4/1981 | France | 128/207.15 |
| 1447987 | 9/1976 | United Kingdom | 128/204.25 |

OTHER PUBLICATIONS

"Heat Sink Protection for Endotracheal Tube Cuff-$_s$CO$_2$ Laser", LeJeune, Jr. et al., American Broncho—Esophagological Assc 5/4/82.
"Lanz" Endotracheal Tube, Extra corporeal Medical Specialties Inc.
"Tracheoplast–Plastic Endotracheal Katheter", Litton Steinmed of Germany.

Primary Examiner—Henry J. Recla
Assistant Examiner—Karin M. Reichle
Attorney, Agent, or Firm—Quarles & Brady

[57] ABSTRACT

A catheter such as an endotracheal tube is rendered resistant to laser beam impaction by coating the cuff and/or the tube with a laser-reflective compound which is preferably comprised of one to three parts of powdered aluminum to one part silicone rubber solution. The laser-reflective compound may be permanently bonded to the cuff and/or the tube by first dipping the cuff and/or the tube in a bath of the compound to form a smooth outer coating on the cuff and/or the tube and then baking the cuff and/or the tube to cure the coating. The laser-reflective coating serves to reflect the laser beam, thus making the catheter laser resistant while the smoothness of the coating aids in catheter insertion.

3 Claims, 3 Drawing Figures

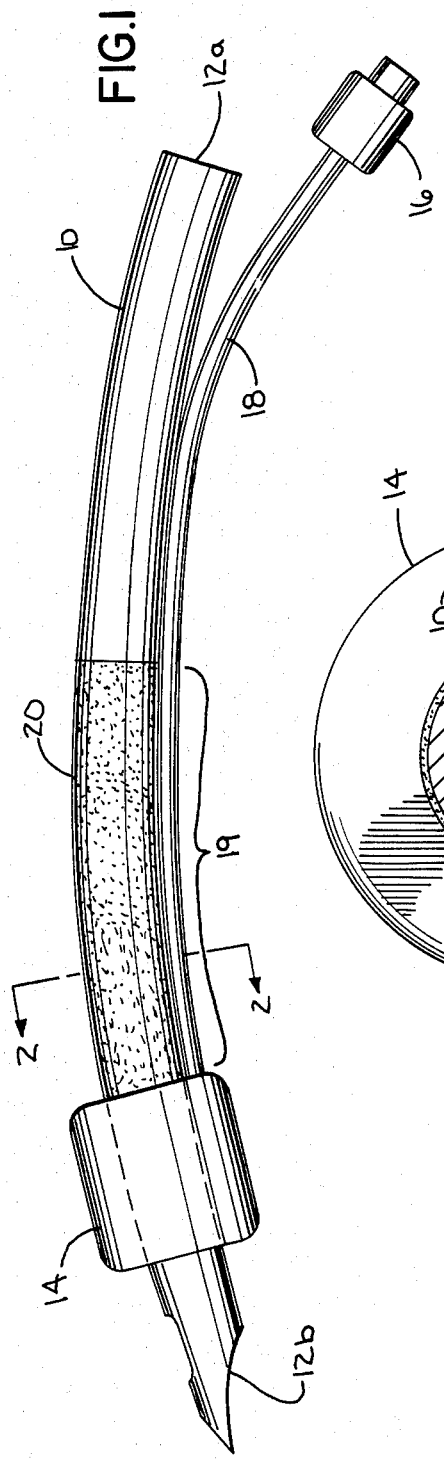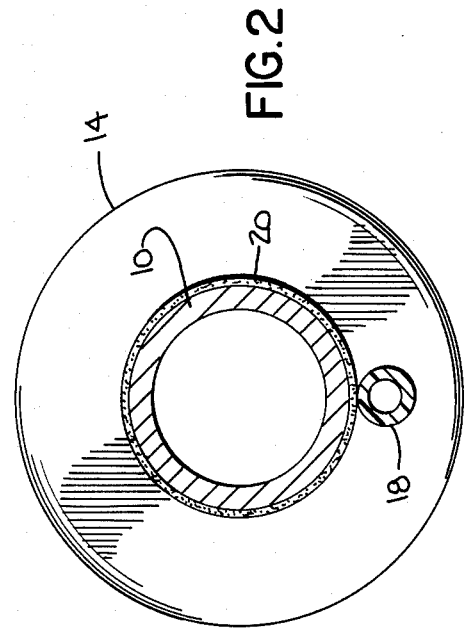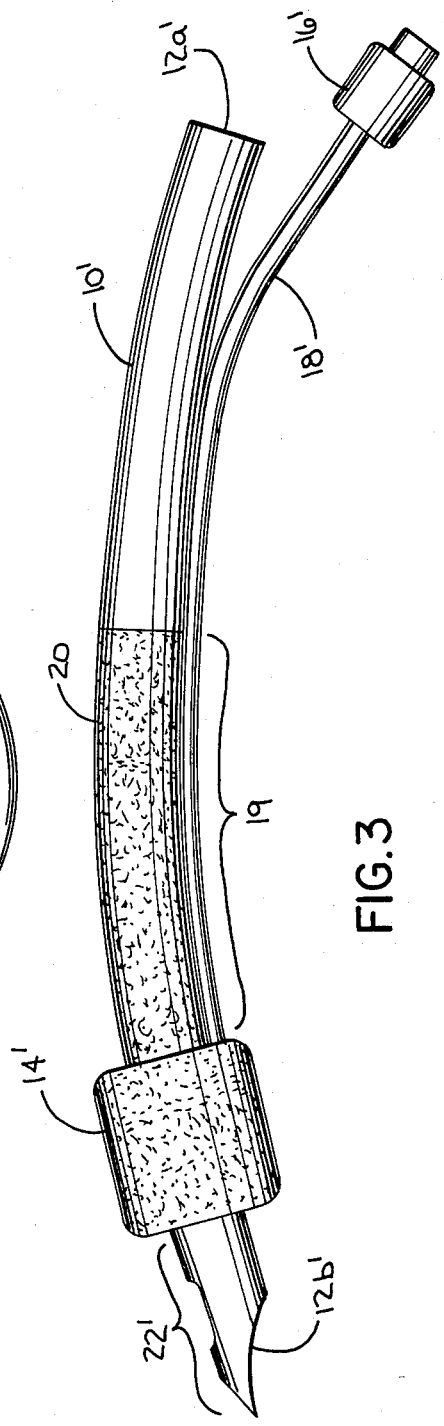

LASER RESISTANT ENDOTRACHEAL TUBE

FIELD OF THE INVENTION

This invention relates generally to catheters, and more particularly to laser resistant catheters for use during laser surgery.

BACKGROUND OF THE INVENTION

During certain medical procedures and especially during surgery, it may be necessary to admit or remove fluids (either liquids or gases) from the patient and a catheter is often employed carrying such fluids. For example during surgery of the throat, a mixture of oxygen and anesthesia usually must be carried into the lungs and a special type of catheter, known as an endotracheal tube, is employed for this purpose. Endotracheal tubes are well known in the art and generally consist of a flexible tube made from silicone rubber, latex rubber or polyvinyl chloride. Usually an inflatable cuff is carried on the tube proximate its distal end, and when inflated, the cuff serves to retain the endotracheal tube in position.

Although present day silicone rubber, latex rubber and polyvinyl chloride endotracheal tubes have proven safe and reliable, use of silicone rubber, latex rubber and polyvinyl chloride endotracheal tubes often presents a serious risk of hazard if used during laser surgery unless the tube is protected against inadvertent laser impaction. Inadvertent laser impaction of an unprotected endotracheal tube will likely cause tube combustion which presents a very serious danger especially if the endotracheal tube were carrying oxygen into the lungs, which is often the case. In the past, endotracheal tubes used during laser surgery have been protected against inadvertent laser impaction by wrapping the tube with a self-adhering metal foil which thus serves to reflect the laser beam should the laser inadvertently impact the endotracheal tube. However, several disadvantages are believed to be associated with this method of protecting the endotracheal tube. Firstly, a certain amount of preparation time is consumed in wrapping a standard endotracheal tube with relfective foil. During emergency situations, there may be insufficient time to perform this task. Secondly, and more importantly, the metal foil on the external tube surface usually presents a rough surface, particularly if the foil is wrapped about the tube so as to overlap itself as is often the case. The presence of a rough surface on the tube will likely impede endotracheal tube intubation and may result in tissue trauma.

In contrast to the endotracheal tubes of the prior art, the present invention concerns an improved laser-resistant endotracheal tube which is not subject to the above enumerated disadvantages.

It is an object of the present invention to provide an improved laser-resistant endotracheal tube;

It is yet another object of the present invention to provide an improved laser-resistant endotracheal tube having a smooth exterior surface to facilitate endotracheal tube intubation;

It is yet another object of the present invention to provide an improved laser-resistant endotracheal tube which requires no special preparation for use during laser surgery.

BRIEF SUMMARY OF THE INVENTION

Briefly, in accordance with the preferred embodiment of the invention, an improved laser-resistant catheter especially adapted for use during laser surgery includes a fluid carrying conduit which typically takes the form of an endotracheal tube having an opening at either end thereof. An inflatable cuff is carried on the tube adjacent to its distal end for retaining the endotracheal tube in place during use. A smooth, laser-reflective coating, typically formulated by adding a reflective material, preferably a powdered metal such as aluminum, to an elastomer solution such as a silicone rubber solution (preferably in the ratio of 1 to 3 parts aluminum to one part silicone rubber solution) is applied to the endotracheal tube so as to surround the tube and cuff. The reflective material (e.g. powdered aluminum) within the coating surrounding the endotracheal tube reflects the laser light so as to protect the tube against laser impaction while the silicone rubber solution provides a nonirritating surface so as to enable easy endotracheal tube intubation.

Typically, the reflective material-silicone rubber solution coating compound is applied to the tube by dipping the tube in the compound or by painting the compound on the tube and then baking the tube to a predetermined temperature to cure the compound. These two steps are repeated until the laser reflective coating reaches a prescribed thickness. The baking step could be eliminated if a room temperature vulcanizing elastomer solution were employed. Once applied to the tube in this fashion, the laser reflective coating remains on the tube permanently.

BRIEF SUMMARY OF THE DRAWING

Features of the present invention believed to be novel are set forth with particularity in the appended claims. The invention itself, however, both as to organization and method of operation, together with further objects and advantages thereof may best be understood by reference to the following description taken in accordance with the accompanying drawings in which:

FIG. 1 is a perspective view of a laser-resistant endotracheal tube in accordance with the teachings of the present invention;

FIG. 2 is a cross-sectional view of the endotracheal tube of FIG. 1 taken along lines 2—2 thereof; and FIG. 3 is a perspective view of an alternate preferred embodiment of a laser-resistant endotracheal tube.

DETAILED DESCRIPTION OF THE PREFERRED EMBODIMENT

Referring to the figures, FIGS. 1 and 2 illustrate a catheter 10 which is especially adapted for use during laser surgery because of the ability of the exterior surface of the catheter to reflect the laser beam, thereby greatly reducing the risk of catheter combustion as a result of laser beam impaction. In the presently preferred embodiment, catheter 10 takes the form of an endotracheal tube having a separate one of openings 12a and 12b at either end thereof. Opening 12b is typically bias cut or chamfered to enable easy insertion of the endotracheal tube 10 into the trachea. An elastomeric cuff 14 is carried on the tube proximate to opening 12b. When tube 10 is inserted into the trachea, cuff 14 is inflated from bulb 16 through a tube 18 so as to expand. Once expanded, the cuff retains the endotracheal tube in position as well as sealing the trachea above the location of the cuff.

Endotracheal tube 10 and cuff 14 are each manufactured from a smooth flexible material, typically silicone or latex rubber or plastic such as polyvinyl chloride. Silicone rubber is preferred because of its higher flash point and relatively inert combustion products. While endotracheal tube manufactured from silicone or latex rubber or polyvinyl chloride have proven safe and reliable, endotracheal tubes manufactured from such materials, and in particular those manufactured from latex rubber or polyvinyl chloride which have a very low flash point, present a serious risk of combustion if the endotracheal tube is inadvertently impacted by the beam of a surgical laser. To render the endotracheal tube resistant to laser impaction, that portion of endotracheal tube 10 likely to be impacted by the laser during surgery, which is typically the 3-4 inch (1-10 cm.) portion 19 of the tube extending from cuff 14 towards opening 12a, is covered with a smooth, laser-reflective coating 20 which tends to reflect the laser beam.

The coating 20, which is applied to portion 19 of the endotracheal tube 10 above cuff 14, comprises a reflective material, preferably a mixture of powdered metal, usually aluminum, and an elastomer solution, usually a silicone rubber solution. The usual ratio of powdered aluminum to silicone sealing solution is 3 to 1 although empirical testing has shown that a coating of 1 part powdered aluminum to one part silicone rubber solution yields satisfactory results. The aluminum within the metallic coating tends to reflect the laser beam, thereby reducing the risk of endotracheal tube combustion. The silicone rubber solution component of the coating 20 causes the coating to be smooth and flexible, thus aiding in endotracheal tube insertion.

During manufacture of endotracheal tube 10, the coating is applied to the tube by first dipping that portion of the tube to be coated into a bath of the coating compound or by painting the tube with the coating compound and then baking the tube with the coating in an oven heated to a sufficient temperature to cure the coating compound. These two steps are repeated until the thickness (which is exaggerated in FIG. 2 for purposes of illustration) reaches a predetermined thickness. Note that the step of baking could in fact be eliminated were a room temperature (RTV) elastomer sealing solution employed. If desired a coat consisting of silicone rubber solution alone can be applied on top of the coating 20.

FIG. 3 illustrates an alternate preferred embodiment 10' of an endotracheal tube constructed in accordance with the teachings of the present invention. Endotracheal tube 10' illustrated in FIG. 3 is constructed much like endotracheal tube 10 of FIG. 1 so that like reference numbers are employed to identify like components of each tube. However, endotracheal tube 10' of FIG. 3 differs from endotracheal tube 10 of FIG. 1 in that endotracheal tube 10' has a smooth, laser-reflective coating 20' which surrounds not only that portion 19' of the endotracheal tube which extends 3-4 inches (7-10 cm.) above cuff 14 but also surrounds tube cuff 14'. The laser-reflective coating may also cover that portion 22' of the tube extending below the cuff. Laser reflective coating 20', like coating 20 of FIG. 1, may be comprised of a mixture of powdered metal, such as aluminum, and an elastomer solution of silicone rubber or the like and is applied to the endotracheal tube 10' in the same manner by which coating 20 is applied to endotracheal tube 10 of FIG. 1.

It is generally more desirable to coat not only that portion 19' of the endotracheal tube 10' above the cuff but also to coat the tube cuff 14' as well as that section 22' of the tube below the cuff, since it is highly probable that the endotracheal tube cuff and that portion of the tube below the cuff may be exposed to laser impaction. Thus by coating substantially the entire length of the tube including the cuff with a smooth reflective laser-resistant coating, the risk of endotracheal tube combustion due to laser impaction is much less than if a portion of the tube were left unprotected.

The foregoing describes an improved catheter having a smooth coating covering the tube for reflecting laser beams so as to make the catheter well suited for use during laser surgery.

While only certain preferred features of the invention have been shown by way of illustration, many modifications and changes will occur to those skilled in the art. It is, therefore, to be understood that the appended claims are intended to cover all such modifications and changes as fall within the true spirit of the invention.

What is claimed is:

1. In combination with an endotracheal tube including a fluid carrying conduit having an open proximal end an an open distal end, an elastomeric cuff attached to said tube approximate the distal end thereof and means for inflating said cuff, the improvement comprising:

a smooth, laser-reflective coating covering both that portion of said endotracheal tube which extends from said tube cuff towards said proximal end and said cuff.

2. The invention according to claim 1 wherein said smooth, laser-reflective coating comprises a mixture of an elastomer and a powdered metal.

3. The invention according to claim 1 wherein said smooth, laser-reflective coating comprises a mixture consisting of one to three parts of powdered aluminum to one part silicone rubber.

* * * * *